(12) United States Patent
Isenring et al.

(10) Patent No.: US 6,355,634 B1
(45) Date of Patent: Mar. 12, 2002

(54) AROMATIC COMPOUNDS

(75) Inventors: Hans Peter Isenring, Sissach; Bettina Weiss, Schönbühl, both of (CH)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 08/483,727

(22) Filed: Jun. 7, 1995

Related U.S. Application Data

(62) Division of application No. 08/114,991, filed on Sep. 1, 1993, which is a continuation of application No. 07/979,354, filed on Nov. 20, 1992, now abandoned, which is a continuation of application No. 07/851,595, filed on Mar. 16, 1992, now abandoned, which is a division of application No. 07/706,917, filed on May 29, 1991, now abandoned.

(30) Foreign Application Priority Data

Jun. 5, 1990 (CH) .............................................. 1891/90
Apr. 23, 1991 (CH) .............................................. 1208/91

(51) Int. Cl.$^7$ ........................ A01N 43/84; C07D 279/12
(52) U.S. Cl. .................... 514/227.5; 514/349; 514/357; 514/438; 514/448; 514/450; 514/452; 514/465; 514/466; 514/470; 544/58.1; 546/300; 546/335; 549/72; 549/77; 549/355; 549/362; 549/365; 549/442; 549/466; 549/467

(58) Field of Search .......................... 544/58.1; 546/300, 546/335; 549/72, 77, 355, 362, 365, 442, 466, 467; 514/227.9, 349, 357, 438, 448, 450, 452, 465, 466, 470

(56) References Cited

U.S. PATENT DOCUMENTS 5,346,902 A * 9/1994 Clough et al. ............... 514/269

* cited by examiner

Primary Examiner—Richard L. Raymond
(74) Attorney, Agent, or Firm—Joseph C. Gil

(57) ABSTRACT

The invention relates to novel compounds of the formula

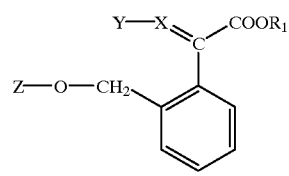

I in which $R_1$ is $C_{1-4}$alkyl and (Y—X) is $CH_2$, $C_{1-2}$alkylthio-CH= or $C_{1-2}$alkyl-ON= and Z is an aldimino or ketimino group, and to their preparation, as well as fungicidal compositions with such compounds as active substances. The compounds can be employed for controlling fungi in agriculture, in horticulture and in wood preservation.

6 Claims, No Drawings

AROMATIC COMPOUNDS

This application is a divisional of application Ser. No. 08/114,991, filed Sep. 1, 1993, which is a continuation of application Ser. No. 07/979,354, filed Nov. 20, 1992, now abandoned, which is a continuation of application Ser. No. 07/851,595, filed Mar. 16, 1992, now abandoned, which is a divisional of application Ser. No. 07/706,917, filed May 29, 1991, now abandoned.

The present invention relates to oxime ethers of the general formula

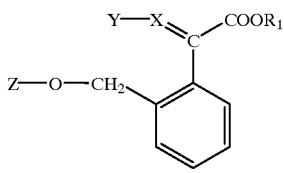

in which $R_1$ is $C_{1-4}$alkyl, (Y—X) is $CH_2$=, $C_{1-2}$alkylthio-CH= or $C_{1-2}$alkyl-ON= and Z is an aldimino or ketimino group, namely in particular a group

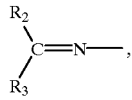

in which $R_2$ is hydrogen, $C_{1-4}$alkyl, $C_{1-4}$haloalkyl, $C_{3-6}$cycloalkyl, $C_{2-4}$alkenyl, $C_{2-4}$alkynyl, $C_{1-2}$alkoxymethyl, $C_{1-2}$alkylthiomethyl, $C_{1-4}$alkylsulfonyl, $C_{1-3}$alkoxy, $C_{1-3}$alkylthio or cyano, and $R_3$ is $C_{1-6}$alkyl, aryl-$C_{1-4}$alkyl, heteroaryl-$C_{1-4}$alkyl, $C_{2-12}$alkenyl, aryl-$C_{2-4}$alkenyl, aryloxy-$C_{1-4}$alkyl, heteroaryloxy-$C_{1-4}$alkyl, heteroaryl-$C_{2-4}$alkenyl, $C_{3-6}$cycloalkyl, aryl, heteroaryl, $C_{2-5}$alkanoyl, aroyl or heteroaroyl, or $R_2$ and $R_3$ together with the carbon atom to which they are bonded form a substituted or unsubstituted four- to seven-membered saturated or unsaturated ring which may contain an oxygen atom, sulfur atom and/or nitrogen atom and which can additionally have a substituted or unsubstituted fused benzene ring.

The compounds according to the invention have fungicidal properties and are suitable as fungicidal active compounds, in particular for use in agriculture and horticulture.

The invention furthermore relates to a process for the preparation of the compounds according to the invention, to fungicidal compositions comprising such compounds as active substances, and to the use of such compounds and compositions for controlling fungi in agriculture and in horticulture.

In a narrower sense, the present invention relates to oxime ethers of the formula I in which $R_1$ is $C_{1-4}$alkyl, (Y—X) is $CH_2$=, $C_{1-2}$alkylthio-CH= or $C_{1-2}$alkyl-ON= and Z is an aldimino or ketimino group, namely in particular a group

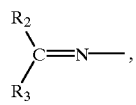

in which $R_2$ is hydrogen, $C_{1-4}$alkyl, $C_{1-4}$haloalkyl or $C_{3-6}$cycloalkyl and $R_3$ is $C_{1-6}$alkyl, aryl-$C_{1-4}$alkyl, heteroaryl-$C_{1-4}$alkyl, $C_{2-6}$alkenyl, aryl-$C_{2-4}$alkenyl, heteroaryl-$C_{2-4}$alkenyl, $C_{3-6}$cycloalkyl, aryl, heteroaryl, $C_{2-5}$alkanoyl, aroyl or heteroaroyl, or $R_2$ and $R_3$ together with the carbon atom to which they are bonded form a substituted or unsubstituted four- to seven-membered saturated ring which may contain an oxygen or sulfur atom and which can additionally have a substituted or unsubstituted fused benzene ring.

In the above formula I and in the following text, all groups "alkyl" and "alkenyl", as such or as part of larger groups, for example heteroarylalkyl, can be straight-chain or branched, depending on the number of carbon atoms. Moreover, the alkenyl groups can have one or more double bonds. Halogen as a substituent is fluorine, chlorine, bromine or iodine, fluorine, chlorine and bromine being preferred. A haloalkyl group can have one or more identical or different halogen substituents. Aryl is understood as meaning, in particular, phenyl, naphthyl, phenanthryl or fluorenyl. Heteroaryl is a heterocyclic group having aromatic character and 1–3 hetero atoms N, O and/or S. Preferred rings are triazole or other five-membered and six-membered rings having 1–2 hetero atoms which, in turn, can additionally have one or two fused benzene rings. Examples which may mentioned and which do not represent any limitation but which, for the sake of simplicity, are referred to as "Het*group" in the following text, are pyrrolyl, pyridyl, furyl, thienyl, isoxazolyl, thiazolyl, pyrazinyl, pyridazinyl, imidazolyl, pyrimidinyl or triazolyl, or such a group with fused benzene, for example quinolinyl, quinoxalinyl, benzofuryl, benzothienyl or dibenzofuryl. This also applies analogously to "aryl" or "heteroaryl" as part of a larger group, for example aralkyl or heteroarylalkyl. Each of the aryl and heteroaryl groups can have one or more of the following substituents: halogen, $C_{1-4}$alkyl, $C_{1-4}$haloalkyl, aryl-$C_{1-4}$alkyl, aryloxy-$C_{1-4}$alkyl, $C_{2-4}$alkenyl, aryl-$C_{2-4}$alkenyl, $C_{2-4}$alkynyl, $C_{3-6}$cycloalkyl, aryl, $C_{1-4}$alkoxy, $C_{1-4}$haloalkoxy, aryl-$C_{1-4}$alkoxy, $C_{1-4}$alkylthio, aryloxy, cyano, nitro, $C_{2-4}$haloalkenyl, $C_{2-4}$haloalkynyl, $C_{2-4}$alkenyloxy, $C_{2-4}$haloalkenyloxy, $C_{3-4}$alkynyloxy, $C_{3-4}$haloalkynyloxy, cyclopropylmethoxy, cyclopropyl (unsubstituted or mono- to trisubstituted by halogen and/or methyl), cyanomethoxy (—OCH$_2$CN), $C_{1-4}$alkoxymethyl, $C_{1-4}$alkylthiomethyl, $C_{1-4}$alkylsulfinylmethyl, $C_{1-4}$alkylsulfonylmethyl, arylthio, thiocyanato, $C_{1-4}$alkoxyiminomethyl, $C_{1-4}$alkanoyloxy and $C_{1-4}$alkoxycarbonyl; and also a heteroaryl radical, a heteroaryl-$C_{1-4}$alkyl radical, a heteroaryloxy-$C_{1-4}$alkyl radical, a heteroaryl-$C_{2-4}$alkenyl radical, a heteroaryl-$C_{1-4}$alkoxy radical or a heteroaryloxy radical; the term heteroaryl being understood as meaning a representative of the abovementioned "Het*group".

Almost all of the abovementioned substituents for aryl and heteroaryl groups can occur once to twice, preferably once, with the exception of $C_{1-4}$alkyl, which is suitable as a substituent up to four times and halogen, which can occur up to three times, and, in the case of fluorine, also up to five times.

The preferred aryl radical is phenyl, whether on its own or as part of another substituent. Accordingly, benzoyl is preferred as aroyl.

$C_2$Alkanoyl is acetyl. Haloalkyl is understood as meaning alkyl groups which are up to hexasubstituted by identical or different substituents from the series comprising F, Cl, Br and/or I. Examples of haloalkyl groups, on their own or as part of another substituent (such as haloalkoxy) are $CH_2Cl$, $CHCl_2$, $CCl_3$, $CHBr_2$, $CH_2CH_2Cl$, $CHCl$—$CHCl_2$, $CF_2Cl$, $CH_2I$, $CF_3$, $C_2F_5$, $CF_2$—$CF_2Cl$, $CHF_2$, $CH_2F$, $CF_2CHFCF_3$.

Trifluoromethyl, difluoromethoxy and trifluoromethoxy are preferred.

Moreover, the aryl groups (in particular phenyl) can carry a five-, six- or seven-membered saturated or unsaturated ring which has one or two oxygen atoms and which can be unsubstituted or mono- or polysubstituted by methyl, methoxy, phenyl, halogen, cyano or oxo (C=O). Examples of such groups are 5-benzofuryl, 6-benzodioxanyl and 5-(1,3-benzodioxolyl).

In the event that $R_2$ and $R_3$ together with the carbon atom to which they are bonded form a substituted or unsubstituted ring as has been described in greater detail above, suitable substituents of the ring

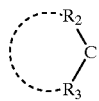

are, in particular, $C_{1-6}$alkyl or substituted or unsubstituted phenyl. It is also possible for the fused benzene ring which may be present to be substituted. Possible substituents of the phenyl group, or of the benzene ring itself, are those mentioned above in connection with the aryl group.

If asymmetric carbon atoms are present in the compounds of the formula I, the compounds exist in optically active form. Merely because of the presence of the aliphatic or imino double bond X=C and the imino double bond of the aldimino or ketimino group Z, the compounds exist in any case in the [E] or [Z] form. Atropisomerism can also occur. The formula I is intended to embrace all these isomeric forms which are possible as well as their mixtures, for example racemic mixtures and any desired [E/Z] mixtures.

In the case of the compounds of the formula I, $R_1$ is preferably methyl; and, independently thereof, (Y—X) is preferably methylene, methylthiomethylene (CH—$SCH_3$) or methoxyimino (N-$OCH_3$); compounds in which $R_1$ is methoxyimino are particularly preferred.

In the group $(R_2)(R_3)C=N$—, $R_2$ is preferably hydrogen, $C_{1-4}$alkyl (in particular methyl or ethyl), $C_{1-4}$haloalkyl (in particular trifluoromethyl) or $C_{3-6}$cycloalkyl (in particular cyclopropyl), and $R_3$ is preferably substituted or unsubstituted phenyl, naphthyl (in particular β-naphthyl) or benzyl, possible substituents preferably being up to three identical or different halogen atoms (in particular fluorine, chlorine and/or bromine), $C_{1-4}$alkyl groups (in particular methyl), $C_{1-4}$haloalkyl groups (in particular trifluoromethyl), $C_{1-4}$haloalkoxy groups (in particular trifluoromethoxy) and alkylenedioxy (in particular 3,4-methylenedioxy), or heteroaryl, in particular furyl which is unsubstituted or substituted by up to two methyl groups, or thienyl, pyridyl or benzofuryl which is unsubstituted or substituted by chlorine or methyl.

In the event that $R_3$ is heteroaryl, $R_2$ is preferably methyl.

Other representatives of compounds of the formula I are:

those compounds of the formula I in which $R_1$ is methyl, (Y—Z) is $CH_2$, Z is a group $(R_2)(R_3)C=N$—, $R_2$ is methyl and $R_3$ is 3-tifluoromethylbenzyl, 4-chloro-3-trifluoromethylbenzyl, 1,4,8-trimethylnona-1,3,7-trienyl, phenyl, 3-chlorophenyl, 4-chlorophenyl, 3-bromophenyl, 3,4-dichlorophenyl, 3,5-dichlorophenyl, 3-nitrophenyl, 4-nitrophenyl, 2-fluoro-5-methylphenyl, 4-methoxyphenyl, 3,4,5-trimethoxyphenyl, 3-trifluoromethoxyphenyl, 3,5-di(trifluoromethyl)phenyl, β-naphthyl, 2-furyl, 2-thienyl, 2-pyridyl, 2-benzofuryl or 5-chloro-2-thienyl;

those compounds of the formula I in which $R_1$ is methyl, (Y—X) is $CH_2$, Z is a group $(R_2)(R_3)C=N$—, $R_3$ is phenyl and $R_2$ is ethyl, propyl or isopropyl;

those compounds of the formula I in which $R_1$ is methyl, (Y—X) is $CH_2$, Z is a group $(R_2)(R_3)C=N$—, $R_2$ is trifluoromethyl and $R_3$ is 2-(β-naphthyl)ethenyl, phenyl, 3-chlorophenyl, 4-chlorophenyl, p-tolyl, α,α,α-trifluoro-m-tolyl, β-naphthyl or 2-pyridyl;

those compounds of the formula I in which $R_1$ is methyl, (Y—X) is $CH_2$, Z is a group $(R_2)(R_3)C=N$—, $R_2$ is cyclopropyl and $R_3$ is phenyl, 3-chlorophenyl, 4-chlorophenyl, 3-bromophenyl, α,α,α-trifluoro-m-tolyl, 4-phenoxyphenyl or β-naphthyl;

those compounds of the formula I in which $R_1$ is methyl, (Y—X) is methylthiomethylene, (=CH—$SCH_3$), Z is a group $(R_2)(R_3)C=N$—, $R_2$ is methyl and $R_3$ is 3-trifluoromethylbenzyl, 4-chloro-3-trifluoromethylbenzyl, 1,4,8-trimethylnona-1,3,7-trienyl, phenyl, 4-fluorophenyl, 3-chlorophenyl, 4-chlorophenyl, 3-bromophenyl, 3,5-dichlorophenyl, 3-nitrophenyl, 4-nitrophenyl, 2-fluoro-5-methylphenyl, 4-methoxyphenyl, 3,4,5-trimethoxyphenyl, 3-trifluoromethoxyphenyl, 3,5-di(trifluoromethyl)phenyl, 2-furyl, 2-benzofuryl or 5-chloro-2-thienyl;

those compounds of the formula I in which $R_1$ is methyl, (Y—X) is methylthiomethylene, Z is a group $(R_2)(R_3)C=N$—, $R_2$ is trifluoromethyl and $R_3$ is 2-(β-naphthyl)ethenyl, phenyl, 3-chlorophenyl, 4-chlorophenyl, p-tolyl, α,α,α-trifluoro-m-tolyl, β-naphthyl or 2-pyridyl;

those compounds of the formula I in which $R_1$ is methyl, (Y—X) is methylthiomethylene, Z is a group $R_2R_3C=N$—, $R_2$ is cyclopropyl and $R_3$ is phenyl, 3-chlorophenyl, 4-chlorophenyl, 3-bromophenyl, α,α, α-trifluoro-m-tolyl, 4-phenoxyphenyl or β-naphthyl;

those compounds of the formula I in which $R_1$ is methyl, (Y—X) is methoxyimino (=N—$OCH_3$), Z is a group $(R_2)(R_3)C=N$—, $R_2$ is methyl and $R_3$ is 4-chloro-3-trifluoromethylbenzyl, phenyl, 3-chlorophenyl, 3,5-dichlorophenyl, 2-fluoro-5-methylphenyl, 3-trifluoromethoxyphenyl or 5-chloro-2-thienyl;

those compounds of the formula I in which $R_1$ is methyl, (Y—X) is methoxyimino, Z is a group $R_2R_3C=N$—, $R_2$ is trifluoromethyl and $R_3$ is 2-(β-naphthyl)ethenyl, phenyl, 3-chlorophenyl, 4-chlorophenyl, p-tolyl, α,α, α-trifluoro-m-tolyl, β-naphthyl or 2-pyridyl;

those compounds of the formula I in which $R_1$ is methyl, (Y—X) is methoxyimino, Z is a group $R_2R_3C=N$—, $R_2$ is cyclopropyl and $R_3$ is 3-chlorophenyl, 4-chlorophenyl, 3-bromophenyl, α,α,α-trifluoro-m-tolyl, 4-phenoxyphenyl or β-naphthyl;

The process according to the invention for the preparation of the compounds of the formula I comprises reacting an oxime Z—OH, in particular an oxime of the general formula

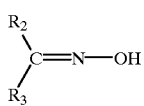

II in which $R_2$ and $R_3$ are as defined above, with a benzyl alcohol derivative of the general formula

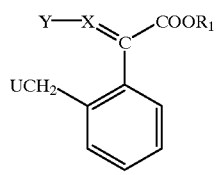

III in which $R_1$ and Y—X are as defined above and U is a leaving group.

This reaction is a nucleophilic substitution, which can be carried out under the reaction conditions which are customary for this type of reaction. The leaving group U in the benzyl alcohol derivative of the formula III is preferably understood as meaning chlorine, bromine, iodine, mesyloxy, benzenesulfonyloxy or tosyloxy. The reaction is expediently carried out in an inert organic diluent such as a cyclic ether, for example tetrahydrofuran or dioxane, acetone, dimethylformamide or dimethyl sulfoxide, in the presence of a base such as sodium hydride, sodium carbonate or potassium carbonate, or a tertiary amine, for example a trialkylamine, in particular diazabicyclononane or diazabicycloundecane, or silver oxide, at temperatures between −20° C. and 80° C., preferably in a temperature range of from 0° C. to 20° C.

Alternatively, the reaction can be effected in an organic solvent, for example methylene chloride, with phase-transfer catalysis, in the presence of an aqueous basic solution, for example sodium hydroxide solution, and in the presence of a phase-transfer catalyst, for example tetrabutylammonium hydrogen sulfate, at room temperature [see, for example, W. E. Keller, "Phasen-Transfer Reactions" [Phase-Transfer Reactions], Fluka-Compendium Vol. I and II, George Thieme Verlag, Stuttgart (1986/1987), in which particular mention is made of Chemistry Letters 1980, pages 869–870].

The compounds of the formula I which have been prepared in this manner can be isolated and purified by methods known per se. Equally, any mixtures of isomers which may have been obtained, for example mixtures of E/Z isomers, can be separated to give the pure isomers, for example by chromatography or fractional crystallisation.

The oximes Z—OH, for example those of the formula II, which are used as starting materials in the process according to the invention are either known or can be prepared by methods known per se, for example by reacting the corresponding carbonyl compound $R_2R_3C=O$ with hydroxylamine chloride in the presence of a base, for example sodium hydroxide or potassium hydroxide or pyridine. More methods can be found in Houben-Weyl, "Methoden der Organischen Chemie" [Methods of Organic Chemistry], Volume X/4, pages 3–308 (1968) "Herstellung und Umwandlung von Oximen" [Preparation and Conversion of Oximes].

Equally, the starting materials of the formula III, i.e. the alkyl α-(2-UCH$_2$-phenyl)-acrylates of the formula IIIa, the alkyl α-(2-UCH$_2$-phenyl)-β-(C$_{1-2}$alkylthio)acrylates of the formula IIIb and the alkyl 2-(2-UCH$_2$-phenyl)glyoxylate O—(C$_{1-2}$alkyl)oxime of the formula IIIc

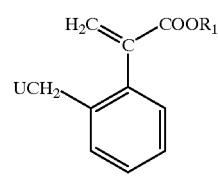

IIIa

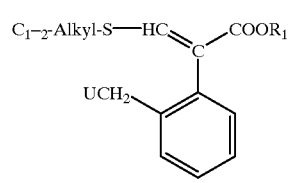

IIIb

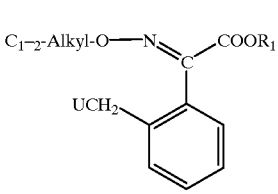

IIIc are either known or can be prepared by methods known per se. For example, European Patent Publication (EP) 348 766 describes the preparation of methyl α-(2-bromomethylphenyl)acrylate, EP 310 954 and Angew. Chem. 71, 349–365 (1959) describe the preparation of methyl α-(2-bromomethylphenyl)-βmethylthioacrylate, and EP 363 818 and also Angew. Chem. 71, 349–365 (1959) describe the preparation of methyl 2-(2-bromomethylphenyl)glyoxylate O-methyloxime. The compounds of the formulae IIIa, IIIb and IIIc, which are novel to date, form a further subject of the present invention.

To prepare a C$_{1-4}$alkyl α-(2-bromomethylphenyl)-β-methylthioacrylate, a synthesis which differs from the process described in EP 310 954 can also be used, which embraces, as the first step, the bromination of the corresponding C$_{1-4}$alkyl 3-(4-bromobenzenesulfonyloxy)-2-(o-tolyl)acrylate with N-bromosuccinimide to give the C$_{1-4}$alkyl 3-(4-bromobenzenesulfonyloxy)-2-(2-bromomethylphenyl)acrylate and, as the second step, the reaction of the last-mentioned ester with sodium methanethiolate to give the desired end product. The starting material methyl 3-(4-bromobenzenesulfonyloxy)-2-(o-tolyl)acrylate is described, for example, in EP 310 954.

The compounds according to the invention have a fungicidal action and can accordingly be used for controlling, or preventing, fungal attack in agriculture, in horticulture and in the protection of wood. They are particularly suitable for inhibiting the growth of or for destroying phytopathogenic fungi on parts of plants, for example leaves, stalks, roots, tubors, fruit or flowers, and on seed, as well as for destroying harmful soil fungi. Furthermore, wood-destroying and wood-discolouring fungi can be controlled using the compounds according to the invention. The compounds according to the invention are effective, for example, in the control of fungi of the classes of the Deuteromycetes, Ascomycetes, Basidiomycetes and phycomycetes.

The compounds according to the invention are particularly suitable for controlling the following pathogens:

Powdery mildews (for example *Erysiphe graminis, Erysiphe cichoracearum, Podosphaera leucotricha, Uncinula necator,* Sphaerotheca spp.)

Rusts (for example *Puccinia tritici, Puccinia recondita, Puccinia hordei, Puccinia coronata, Puccinia striiformis, Puccinia arachidis, Hemileia vastatrix, Uromyces fabae*)

Scabs (for example *Venturia inaequalis*)

Cercospora spp. (for example *Cercospora arachidicola, Cercospora beticola*)

Mycosphaerella spp. (for example *Mycosphaerella fijiensis*)

Alternaria spp. (for example *Alternaria brassicae, Alternaria mali*)

Septoria spp. (for example *Septoria nodorum*)

Helminthosporium spp. (for example *Helminthosporium teres, Helminthosporium oryzea*)

Plasmopara spp. (for example *Plasmopara viticola*)

Pseudoperonospora spp. (for example *Pseudoperonospora cubensis*)

Phytophthora spp. (for example *Phytophthora infestans*)

Pseudocercosporella spp. (for example *Pseudocercosporella herpotrichoides*)

Piricularia spp. (for example *Piricularia oryzae*)

Furthermore, the compounds act for example against fungi of the genera Tilletia, Ustilago, Rhizoctonia, Verticillium, Fusarium, Pythium, Gaeumannomyces, Sclerotinia, Monilia, Botrytis, Peronospora, Bremia, Gloeosporium, Cercosporidium, Penicillium, Ceratocystis, Rhynchosporium, Pyrenophora, Diaporthe, Ramularia and Leptosphaeria. Moreover, certain representatives of the compounds according to the invention have an action against fungi which damage wood, for example those of the genera Coniophora, Gloeophyllum, Poria, Merulius, Trametes, Aureobasidium, Sclerophoma and Trichoderma.

The compounds of the formula I according to the invention are distinguished by a prophylactic and curative, but mainly by a noticeable systemic action.

Under greenhouse conditions, they act against phytopathogenic fungi at concentrations of from as little as 0.5 mg to 500 mg of active substance per litre of spray mixture. In the field, it is advantageous to apply dosage rates of from 20 g to 1 kg of active substance of the formula I per hectare per treatment. To control seed-borne or soil-borne fungi by the seed-dressing method, it is advantageous to use dosage rates of from 0.001 g to 1.0 g of active substance of the formula I per kg of seed.

The compounds according to the invention can be formulated to give various compositions, for example solutions, suspensions, emulsions, emulsifiable concentrates and preparations in the form of powders. The fungicidal compositions according to the invention comprise an effective amount of at least one compound of the general formula I, as defined above, as well as formulation auxiliaries. The compositions advantageously comprise at least one of the following formulation auxiliaries:

solid carriers; solvents or dispersants; surfactants (wetting agents and emulsifiers); dispersants (without surfactant action); and stabilisers.

As solid carriers, the following are mainly suitable: natural mineral substances, such as kaolin, clays, kieselguhr, talc, bentonite, chalk, for example whiting, magnesium carbonate, limestone, quartz, dolomite, attapulgite, montmorillonite and diatomaceous earth; synthetic mineral substances, such as highly-disperse silica, aluminium oxide and silicates; organic substances, such as cellulose, starch, urea and synthetic resins; and fertilisers, such as phosphates and nitrates, it being possible for such carriers to be, for example, in the form of granules or powders.

As solvents or dispersants, the following are mainly suitable: aromatics, such as toluene, xylenes, benzene and alkylnaphthalenes; chlorinated aromatics and chlorinated aliphatic hydrocarbons, such as chlorobenzenes, chloroethylenes and methylene chloride; aliphatic hydrocarbons, such as cyclohexane and paraffins, for example mineral oil fractions; alcohols, such as butanol and glycol, as well as their ethers and esters; ketones, such as acetone, methyl ethyl ketone, methyl isobutyl ketone and cyclohexanone; and strongly polar solvents and dispersants such as dimethylformamide, N-methylpyrrolidone and dimethyl sulfoxide, such solvents and dispersants preferably having flash points of at least 30° C. and boiling points of at least 50° C., and water. Amongst the solvents or dispersants, so-called liquefied gaseous extenders or carriers, which are products which are gaseous at room temperature and under atmospheric pressure, are also suitable. Examples of such products are, in particular, aerosol propellants, such as (halo)hydrocarbons. In the event that water is used as solvent, it is also possible for, for example, organic solvents to be used as auxiliary solvents.

The surfactants (wetting agents and emulsifiers) can be nonionic compounds, such as condensation products of fatty acids, fatty alcohols or fatty-substituted phenols with ethylene oxide; fatty acid esters and fatty acid ethers of sugars or polyhydric alcohols; the products obtained from sugars or polyhydric alcohols by condensation with ethylene oxide; block copolymers of ethylene oxide with propylene oxide; or alkyldimethylamine oxides.

The surfactants can also represent anionic compounds, such as soaps; fatty sulfate esters, for example dodecyl sodium sulfate, octadecyl sodium sulfate and cetyl sodium sulfate; alkylsulfonates, arylsulfonates and fatty-aromatic sulfonates, such as alkylbenzenesulfonates, for example calcium dodecylbenzenesulfonate, and butylnaphthalenesulfonate; and more complex fatty sulfonates, for example the amide condensation products of oleic acid and N-methyltaurine, and the sodium sulfonate of dioctyl succinate.

Finally, the surfactants can be cationic compounds, such as alkyldimethyl-benzylammonium chlorides, dialkyldimethylammonium chlorides, alkyltrimethylammonium chlorides and ethoxylated quaternary ammonium chlorides.

As dispersants (without surfactant action) the following are mainly suitable: lignin, sodium salts and ammonium salts of ligninsulfonic acid, sodium salts of maleic anhydride/diisobutylene copolymers, sodium salts and ammonium salts of sulfonated polycondensation products of naphthalene and formaldehyde, and sulfite waste liquors.

Examples of dispersants which can be employed and are particularly suitable as thickeners or anti-settling agents are methylcellulose, carboxymethylcellulose, hydroxyethylcellulose, polyvinyl alcohol, alginates, caseinates and blood albumin.

Examples of suitable stabilisers are acid-binding agents, for example epichlorohydrin, phenyl glycidyl ether and soya epoxides; antioxidants, for example gallic esters and butylhydroxytoluene; UV absorbers, for example substituted benzophenones, diphenylacrylonitrile acid esters and cinnamic esters; and deactivators, for example salts of ethylenediaminetetraacetic acid, and polyglycols.

Besides the active compounds of the formula I, the fungicidal compositions according to the invention can also comprise other active compounds, for example other types of fungicidal compositions, insecticidal and acaricidal compositions, bactericides, plant growth regulators and fertilisers. Such combination compositions are suitable for broadening the spectrum of action or for specifically influencing plant growth.

In general, the compositions according to the invention comprise between 0.0001 and 85 percent by weight of a compound or compounds according to the invention as active substance(s), depending on the nature of these compositions. They can be in a form which is suitable for storage and transport. In such forms, for example emulsifiable concentrates, the concentration of active substance is usually in the higher range of the above concentration interval. These forms can then be diluted with identical or different formulation auxiliaries to concentrations of active substance which are suitable for use in practice, and such concentrations are usually in the lower range of the above concentration interval. Emulsifiable concentrates generally comprise 5 to 85 percent by weight, preferably 25 to 75 percent by weight, of the compound(s) according to the invention. Suitable as use forms are, inter alia, ready-for-use solutions, emulsions and suspensions, which are suitable, for example, as spray mixtures. The concentrations in such spray mixtures can be, for example, between 0.0001 and 20 percent by weight. In the ultra-low volume method, it is possible to formulate spray mixtures in which the concentration of active substance is preferably from 0.5 to 20 percent by weight, while the concentration of active substance in the spray mixtures formulated in the low-volume method and in the high-volume method is preferably from 0.02 to 1.0, or 0.002 to 0.1, percent by weight.

The fungicidal compositions according to the invention can be prepared by mixing at least one compound according to the invention with formulation auxiliaries.

The compositions can be prepared in a known manner, for example by mixing the active substances with solid carriers, by dissolving or suspending them in suitable solvents or dispersants, if appropriate with the use of surfactants as wetting agents or emulsifiers, or of dispersants, by diluting pre-prepared emulsifiable concentrates with solvents or dispersants, etc.

In the case of compositions in the form of powders, the active substance can be mixed with a solid carrier, for example by concomitant grinding; or the solid carrier can be impregnated with a solution or suspension of the active substance, and the solvent or dispersant can then be removed by evaporation, heating or by filtering off with suction under reduced pressure. By adding surfactants or dispersants, it is possible to make such compositions in the form of powders readily wettable with water, so that they can be converted into aqueous suspensions which are suitable, for example, as spray liquors.

Alternatively, the compounds according to the invention can be mixed with a surfactant and a solid carrier to form a wettable powder which is dispersible in water, or they can be mixed with a solid pregranulated carrier to form a product in the form of granules.

If desired, a compound according to the invention can be dissolved in a solvent which is not miscible with water, for example an alicyclic ketone, which advantageously contains dissolved emulsifier, so that the solution is self-emulsifying when added to water. On the other hand, the active substance can be mixed with an emulsifier, and the mixture can then be diluted with water to the desired concentration. Moreover, the active substance can be dissolved in a solvent and the solution can then be mixed with an emulsifier. Such a mixture can equally be diluted with water to the desired concentration. In this manner, emulsifiable concentrates, or ready-for-use emulsions, are obtained.

The compositions according to the invention can be used by the application methods customary in crop protection or in agriculture. The process according to the invention for controlling fungi comprises treating the locus to be protected or the goods to be protected, for example plants, parts of plants, or seeds, with an effective amount of a compound according to the invention, or a composition according to the invention.

The examples which follow illustrate the invention.

I. Preparation of the Active Compound of the Formula I:

EXAMPLE 1

0.637 g of methyl 2-(2-bromomethylphenyl)acrylate as well as 0.5 g of 3-trifluoromethylacetophenone oxime in 2 ml of dimethylformamide are added dropwise at 5–10° C. to a suspension of 0.24 g of sodium hydride (55–60% in oil) in 20 ml of dimethylformamide, while passing in argon. The reaction mixture is stirred for a further 30 minutes. When the reaction has ended, the mixture is poured into water, and the aqueous mixture is extracted using three portions of ethyl acetate. The combined organic phases are washed twice with water, dried over anhydrous sodium sulfate and evaporated under reduced pressure. The oil which remains is then purified by chromatography on silica gel using n-hexane/methylene chloride (1:1) as the mobile phase.

In this manner, methyl 2-[α-{-[(E/Z-α-methyl-3-trifluoromethylbenzyl)imino]oxy}-o-tolyl]acrylate is obtained as a colourless oil. (MS: 377(4); 115)

EXAMPLE 2

1.27 g of methyl 2-(2-bromomethylphenyl)acrylate and 0.94 g of 4-phenylcyclohexanone oxime are added to a two-phase mixture of 30 ml of methylene chloride and 30 ml of 2.2 N sodium hydroxide solution, containing 4.38 g of tetrabutylammonium hydrogen sulfate as phase-transfer catalyst. The mixture is then stirred vigorously for 30 minutes. When the reaction is complete, the organic phase is separated off and dried over anhydrous sodium sulfate, and the organic solvent is distilled off. The oil which remains is purified by chromatography on silica gel using ethyl acetate/n-hexane (1:9) as the mobile phase.

In this way, methyl 2-[α-{[(4-phenylcyclohexylidene)amino]oxy)}-o-tolyl]acrylate is obtained as a yellow oil. (MS: 363(5); 115)

EXAMPLE 3

1 g of methyl α-(2-bromomethylphenyl)-β-methylthioacrylate and 0.67 g of 3-trifluoromethylacetophenone oxime are added to a two-phase mixture of 3 ml of methylene chloride and 3 ml of 2.2 N sodium hydroxide solution, containing 1.5 g of tetrabutylammonium hydrogen sulfate as phase-transfer catalyst. The reaction mixture is stirred vigorously at room temperature for approximately 15 minutes. The same amounts of methylene chloride, 2.2 N sodium hydroxide solution and tetrabutylammonium hydrogen sulfate are then added, and stirring is continued for a further 15 minutes. When the reaction is complete, the mixture is rendered neutral using saturated sodium hydrogen carbonate solution, and the organic phase is separated off, washed three times with water and dried over anhydrous sodium sulfate. After the organic solvent has been distilled off, the oil which remains is purified by chromatography on silica gel using diethyl ether/n-hexane (1:1) as the mobile phase.

In this manner, methyl 2-[α-{[(α-methyl-3-trifluoromethylbenzyl)imino]oxy}-o-tolyl]-3-methylthioacrylate is obtained as a yellow oil. (MS: 376 (30); 161).

EXAMPLE 4

5 g of methyl 2-(2-bromomethylphenyl)glyoxylate O-methyl oxime and 3.2 g of β-acetonaphthone oxime in 80 ml of dimethylformamide are added dropwise at 0° C. to a suspension of 0.78 g of sodium hydride (80% in oil) in 20 ml of dimethylformamide, while passing in argon gas, and stirring of the reaction mixture is continued for 4 hours at 0° C. When the reaction is complete, the mixture is hydrolysed using saturated ammonium chloride solution and extracted three times using diethyl ether. The combined organic phases are dried over anhydrous sodium sulfate, and the solvent is distilled off. The oil which remains is purified by chromatography on silica gel using diethyl ether/n-hexane (1:1) as the eluent, and the product is crystallised from methylene chloride/diethyl ether/n-hexane.

In this manner, methyl 2-[α-{[(1-[β-naphthyl]ethyl)imino]oxy}-o-tolyl]glyoxylate O-methyl oxime is obtained as white crystals, m.p. 97–98° C. (MS: 390(4); 116)

EXAMPLES 5–41

Compounds 5 to 11 of formula I, which are mentioned in the table below and are obtained as an oil, are obtained from the corresponding o-substituted benzyl bromide of the formula III (U=Br) and the corresponding oxime of the formula II analogously to the method described in Example 1 ("method 1"), Example 2 ("method 2"), Example 3 ("method 3") and Example 4 ("method 4").

These compounds, as well as the compounds of Examples 1 to 4, are characterised by selected values of their mass spectrum: the first value corresponds to the highest mass number. The second value corresponds to the basis peak. The intensity of the signal with the highest mass number appears in brackets as a percentage, relative to the basis peak (=100%).

TABLE 1

| Example | Y-X | $R_2$ | $R_3$ | Physical data (MS) | Method 1/2/3/4 |
|---|---|---|---|---|---|
| 5 | $CH_2$ | H | 4-chlorophenyl | 329(1); 115 | 1 |
| 6 | $CH_2$ | H | phenyl | 295(2); 115 | 2 |
| 7 | $CH_2$ | | 4-tert-butyl-cyclohexylidene | 343(6); 115 | 2 |
| 7a | $CH_2$ | $CH_3$ | 3,4-methylene-dioxyphenyl | 353(6); 115 | 1 |
| 8 | $CH_3S$—CH | $CH_3$ | 3,4-dichlorophenyl | 424(2); 161 | 3 |
| 9 | $CH_3S$—CH | $CH_3$ | β-naphthyl | 405(1); 161 | 3 |
| 10 | $CH_3S$—CH | $CH_3$ | 2-thienyl | 314(29); 161 | 3 |
| 11 | $CH_3S$—CH | $CH_3$ | 2-pyridyl | 356(<0.5); 161 | 3 |

The following methoximinoglyoxylic acid derivatives of Table 2, which are obtained, mainly by method 4, in form of solids or oils are characterised by melting point and/or MS (=mass spectrum):

TABLE 2

$$\text{structure with } R_2R_3C=N-O-CH_2\text{-phenyl-}C(=N-OCH_3)COOCH_3$$

| Example | R₂ | R₃ | | Physical data |
|---|---|---|---|---|
| 12 | CH₃ | α,α,α-trifluoro-m-tolyl | oil | 408(<0.5); 186 |
| 13 | CH₃ | 3,4-dichlorophenyl | | m.p. 1.3–105° C. |
| 14 | CH₃ | 2-thienyl | oil | 346(2); 116 |
| 15 | CH₃ | 2-pyridyl | | m.p. 82–84° C. |
| 16 | | 1,2,3,4-tetrahydro-α-naphthylidene | oil | 366(1); 116 |
| 17 | CH₃ | 4-chlorophenyl | cryst. | 343(2); 116 |
| 18 | n-propyl | phenyl | cryst. | 368(<0.5); 116 |
| 19 | CH₃ | 4-methoxyphenyl | cryst. | 370(10); 116 |
| 20 | CH₃ | 3,4,5-trimethoxyphenyl | oil | 430(49); 116 |
| 21 | CH₃ | 2-furyl | | m.p. 95–97° C. |
| 22 | CH₃ | 3-bromophenyl | cryst. | 389(0.5); 116 |
| 23 | CH₃ | 1,4,8-trimethylnona-1,3,7-trienyl | oil | 426(2); 116 |
| 24 | CH₃ | 3-trifluoromethylbenzyl | oil | 422(4); 116 |
| 25 | CH₃ | 4-nitrophenyl | cryst. | 354(1); 116 |
| 26 | CH₃ | 3-nitrophenyl | cryst. | 354(0.5); 116 |
| 27 | CF₃ | phenyl | cryst. | 222(4); 116 |
| 28 | CH₃CH₂— | phenyl | oil | 323(2); 116 |
| 29 | i-propyl | phenyl | oil | 368(1); 116 |
| 30 | CF₃ | 3-bromophenyl | oil | 252(2); 116 |
| 31 | CF₃ | 4-tolyl | cryst. | 222(6); 116 |
| 32 | CH₃ | 2-benzofuryl | | m.p. 110–112° C. |
| 33 | CH₃ | 3,5-di(trifluoromethyl)phenyl | | m.p. 76–78° C. |
| 34 | CH₃ | 4-fluorophenyl | | m.p. 89–90° C. |
| 35 | CH₃O—CH₂— | β-naphthyl | oil | 420(4); 45 |
| 36 | cyclopropyl | phenyl | oil | 355(3); 116 |
| 37 | CH₃ | 1-phenoxyethyl | cryst. | 291(63); 116 |
| 38 | CH₃ | 3,4-methylenedioxyphenyl | oil | 384(12); 116 |
| 39 | CF₃ | 3-trifluoromethylphenyl | oil | 240(3); 116 |
| 40 | CH₃ | 3-fluorophenyl | | |
| 41 | cyclopropyl | 3,4-methylenedioxyphenyl | | |
| 42 | iospropyl | 3,4-methylenedioxyphenyl | | |
| 43 | CH₃ | 6-(1,4-benzodioxanyl) | | |
| 44 | cyclopropyl | 6-(1,4-benzodioxanyl) | | |
| 45 | CH₃ | 3,4-(difluoromethylenedioxy)phenyl | | |
| 46 | CH₃ | 3,4-(difluoromethylenedioxy)benzyl | | |
| 47 | CH₃ | 3,4-ethylenedioxybenzyl | | |
| 48 | CH₃ | 2,3-(difluoromethylenedioxy)phenyl | | |
| 49 | CH₃ | 4-methoxy-3-(methylthiomethyl)phenyl | | |
| 50 | CH₃ | 2,2,3-trifluoro-7-methyl-1,4-benzodioxan-3-yl | | |
| 51 | CH₃ | 3-chloro-5-trifluoromethyl-2-(m-tolyloxy)pyridin-6-yl | | |
| 52 | | 3-(m-CF₃,p-Cl-phenyl)-5,6-dihydro-1,4-thiazin-2-ylidene | | |
| 53 | | 3-(p-Cl-phenyl)-5,6-dihydro-1,4-thiazin-2-ylidene | | |

TABLE 2-continued $$\text{structure with } R_2, R_3, \text{C=N-O-CH}_2\text{-phenyl-C(=N-OCH}_3\text{)-COOCH}_3$$

| Example | R₂ | R₃ | Physical data |
|---|---|---|---|
| 54 | CH₃ | 3,4-methylenedioxybenzyl | |
| 55 | CH₃ | 6-nitro-3,4-(methylenedioxy)phenyl | |
| 56 | H | 3,4-(difluoromethylenedioxy)phenyl | |
| 57 | CH₃ | 2-(3,4-methylenedioxyphenyl)ethenyl | |
| 58 | CH₃ | 2-(3,4-methylenedioxyphenyl)ethyl | |
| 59 | CH₃ | 4-methoxy-3-(methylsulfinylmethyl)phenyl | |
| 60 | CH₃ | 4-methoxy-3-(methylsulfonylmethyl)phenyl | |
| 61 | CH₃ | 3,4-propylenedioxyphenyl | |
| 62 | CH₃ | 2,2-dimethyl-5-methyl-benzo[1,3]dioxole | |
| 63 | CH₃ | benzo[1,3]dioxol-5-yl-OCH₂- | |
| 64 | CH₃ | 3,4-methylenedioxybenzoyl | |
| 65 | CH₃ | 8-methoxy-6-methyl-4H-benzo[1,3]dioxine | |
| 66 | CH₃ | 3-allyloxyphenyl | |
| 67 | CH₃ | 3-propargyloxyphenyl | |
| 68 | CH₃ | 3-cyclopropylmethoxyphenyl | oil 410(8); 116 |
| 69 | CH₃ | 3-(2,2-dichlorovinyloxy)phenyl | |
| 70 | CH₃ | 3-cyanophenyl | |
| 71 | CH₃ | 3-thiocyanatophenyl | |
| 72 | CH₃ | 4-(2,2-dichlorovinyl)phenyl | |
| 73 | CH₃ | 5-(2-cyanobenzofuryl | |
| 74 | CH₃ | 3-(CH₃ON=CH)-phenyl | |
| 75 | CH₃ | 3-(CH₃OOC)-phenyl | |
| 76 | CH₃ | 2-phenyl-5-methyl-benzo[1,3]dioxole | |
| 77 | H | 5-(1-chloro-2-methylpropen-1-yl)-benzo[1,3]dioxole | |

TABLE 2-continued

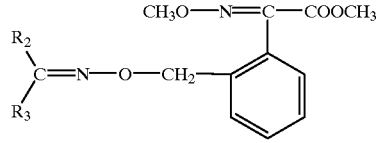

| Example | $R_2$ | $R_3$ | Physical data |
|---|---|---|---|
| 78 | $CH_3$ | 4-difluoromethoxyphenyl | |
| 79 | $CH_3$ | 3-acetoxyphenyl | |
| 80 | $CH_3$ | 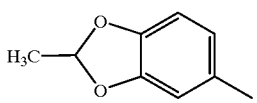 | |
| 81 | $CH_3$ | 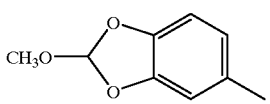 | |
| 82 | $CH_3$ | 4-methoxy-3-nitrophenyl | |
| 83 | $CH_3$ | 4-methoxy-3-(methoxymethyl)phenyl | |
| 84 | $CH_3$ | 3-allyloxy-4-methoxyphenyl | |
| 85 | $CH_3$ | 3-ethoxy-4-methoxyphenyl | |
| 86 | $CH_3$ | 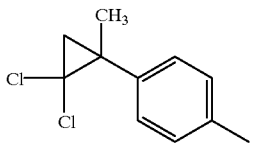 | oil |
| 87 | $CH_3$ | 3-(2,5-dimethylthienyl) | |
| 88 | $CH_3$ | 2-(5-methylthienyl) | |
| 89 | cyclopropyl | 4-fluorophenyl | |
| 90 | $CH_3$ | 4-fluoro-3-trifluoromethylphenyl | |
| 91 | H | 3-nitrophenyl | |
| 92 | $CH_3$ | 3-cyanomethoxyphenyl | |
| 93 | $CH_3$ | 4-fluoro-3-phenoxyphenyl | |
| 94 | $CH_3$ | 4-thioCyanato-3-trifluormethylphenyl | |
| 95 | $CH_3CH=CH$ | 3,4-methylenedioxyphenyl | |
| 96 | CN | 3,4-methylenedioxyphenyl | |
| 97 | $CH_3SO_2$ | 3,4-methylenedioxyphenyl | |
| 98 | $CH_3CH_2$ | 3,4-(difluoromethylenedioxy)phenyl | |
| 99 | $CH_3CH_2CH_2$ | 3,4-(difluoromethylenedioxy)phenyl | |
| 100 | isopropyl | 3,4-(difluoromethylenedioxy)phenyl | |
| 101 | cyclopropyl | 3,4-(difluoromethylenedioxy)phenyl | |
| 102 | $CH_3OCH_2$ | 3,4-(difluoromethylenedioxy)phenyl | |
| 103 | $CH_3$ | 1-(3,4-methylenedioxyphenyl)ethyl | |
| 104 | H | 1-methyl-1-(3,4-methylenedioxyphenyl)ethyl | |
| 105 | H | 2-thienOyl | |
| 106 | $CH_3$ | 4-(pentafluoroethoxy)phenyl | |
| 107 | $CH_3$ | 4-(2,2,2-tifluoroethoxy)phenyl | oil |
| 108 | $CH_3$ | 4-(1,1,2,3,3,3-hexafluoropropoxy)phenyl | |
| 109 | $CH_3SCH_2$ | 3,4-methylenedioxyphenyl | |
| 110 | $CH_3CH_2$ | 2-thienyl | |
| 111 | $CH_3CH_2CH_2$ | 4-tolyl | |
| 112 | $CH_3$ | 4-chloro-2-methoxyphenyl | |
| 113 | $CH_3CH=CH$ | 3-trifluoromethylphenyl | |

TABLE 2-continued

Structure: R2R3C=N-O-CH2-(2-substituted phenyl with CH3O-N=C(COOCH3)- group)

| Example | R₂ | R₃ | Physical data |
|---|---|---|---|
| 114 | H | 3,4-methylenedioxyphenyl-CH=C(CH₃)- | |
| 115 | CH₃ | 5-methyl-2(3H)-benzofuranon-3-yl | |
| 116 | CH₃ | 5-methyl-3-oxo-2,3-dihydrobenzofuran-2-yl | |
| 117 | CH₃ | 6-methyl-4H-1,3-benzodioxin-2-yl | |
| 118 | CH₃ | 3,3-dimethyl-8-methyl-2,3,4,5-tetrahydro-1,5-benzodioxepin-2-yl | |
| 119 | CH₃ | 6-methoxy-β-naphthyl | |
| 120 | CH₃CH₂ | β-naphthyl | |
| 121 | CH₃CH₂CH₂ | β-naphthyl | |
| 122 | isopropyl | β-naphthyl | |
| 123 | tert-butyl | β-naphthyl | |
| 124 | CH₃S | phenyl | oil |
| 125 | CH₃S | 4-chlorophenyl | |
| 126 | CH₃S | 3-trifluoromethylphenyl | |
| 127 | CH₃O | 4-chlorophenyl | |
| 128 | CH₃ | 4-fluorobenzoyl | |
| 129 | CH₃ | 3-bromobenzoyl | |
| 130 | CH₃ | 3-nitrobenzoyl | |
| 131 | CH₃ | 3-trifluoromethylbenzoyl | |
| 132 | CH₃ | 2-toluoyl | |
| 133 | CH₃ | 4-chloro-3-trifluoromethylbenzyl | |
| 134 | CH₃ | phenyl | |
| 135 | CH₃ | 3-chlorophenyl | |
| 136 | CH₃ | 3,5-dichlorophenyl | |
| 137 | CH₃ | 6-fluoro-3-tolyl | |
| 138 | CH₃ | 3-trifluoromethoxyphenyl | oil 425(1); 116 |
| 139 | CH₃ | 2-(5-chlorothienyl) | |
| 140 | CF₃ | 2-(β-naphthyl)ethenyl | |
| 141 | CF₃ | 3-chlorophenyl | |
| 142 | CF₃ | 4-chlorophenyl | |
| 143 | CF₃ | β-naphthyl | |
| 144 | CF₃ | 2-pyridyl | |
| 145 | cyclopropyl | 3-chlorophenyl | |
| 146 | cyclopropyl | 4-chlorophenyl | |
| 147 | cyclopropyl | 3-bromophenyl | |
| 148 | cyclopropyl | 3-trifluoromethylphenyl | |
| 149 | cyclopropyl | 4-phenoxyphenyl | |
| 150 | cyclopropyl | β-naphthyl | |

EXAMPLES 151–157

The compounds of the formula I listed in Table 3 below are obtained, in the form of oils, from the corresponding o-substituted benzyl bromide of the formula III (U=Br) and the corresponding oxime of the formula II analogously to the process described in Example 1 ("method 1"):

TABLE 3

$$\underset{R_3}{\overset{R_2}{C}}=N-O-CH_2-\underset{\phantom{C}}{\overset{Y-X}{\underset{\phantom{C}}{C}}}\underset{COOCH_2CH_3}{\phantom{C}}$$

| Example | Y-X | $R_2$ | $R_3$ | Physical data (MS) |
|---|---|---|---|---|
| 151 | $CH_2$ | $CH_3$ | 4-fluorophenyl | 341(3); 115 |
| 152 *) | $CH_2$ | $CH_3$ | 2-thienyl | 329(4); 115 |
| 153 *) | $CH_2$ | $CH_3$ | 2-thienyl | 329(6); 115 |
| 154 | $CH_2$ | $CH_3$ | 3,4-dichlorophenyl | 391(2); 115 |
| 155 | $CH_2$ | $CH_3$ | phenyl | 205(0, 5); 115 |
| 156 | $CH_2$ | $CH_3$ | 4-nitrophenyl | 368(2); 115 |
| 157 | $CH_2$ | $CH_3$ | β-naphthyl | 373(7); 115 |

*) Compounds 152 and 153 are E/Z isomers (not attributed).

Formulation Examples

F1

An emulsifiable concentrate has, for example, the following composition:

|  | mg/litre |
|---|---|
| Active substance of Tables 1 to 3 | 100 |
| Nonylphenol (10)ethoxylate (nonionic emulsifier) | 50 |
| Calcium dodecylbenzenesulfonate (anionic emulsifier) | 25 |
| N-Methyl-2-pyrrolidone (solubiliser) | 200 |
| Mixture of alkylbenzenes (solvent) | to 1 litre |

The active substance and the emulsifiers are dissolved in the solvent and in the solubiliser. By emulsifying this concentrate in water, a ready-for-use spray liquor of any desired dilution can be prepared.

F2

A wettable powder has, for example, the following composition:

|  | Percent by weight |
|---|---|
| Active substance of Tables 1 to 3 | 25.0 |
| Silica (hydrated; carrier) | 20.0 |
| Sodium laurylsulfate (wetting agent) | 2.0 |
| Sodium lignosulfonate (dispersant) | 4.0 |
| Kaolin (carrier) | 49.0 |

The components are mixed with each other and ground finely in a suitable mill. By dispersing the mixture in water, a suspension which is suitable as ready-for-use spray mixture is obtained.

Biological Examples

Example B1

*Puccinia coronata* (Curative Action)

30–40 oat seedlings cv. "Selma" (distributed to 2 pots of ⌀7 cm) are infected with *Puccinia coronata* by spraying with an aqueous spore suspension (approx. 150,000 uredospores/ml). The test plants are subsequently incubated for 24 hours at 20–24° C. and under dew-point conditions. The oat seedlings are then sprayed thoroughly from all sides with a spray mixture prepared with a wettable powder of the active substance (with 160 ppm of active ingredient). They are cultured further in a controlled-environment cabinet at 19° C. and with a photoperiod of 14 hours. The test is evaluated 9–10 days after infection by determining the leaf area infected with *Puccinia coronata* as a percentage compared with the infected, untreated control.

The following compounds, for example, show an action of more than 75% when used at a dosage rate of 160 ppm: 3, 8, 9, 11, 12, 17, 78, 90, 107, 128, 131, 133, 138, 148.

Untreated, but infected control plants showed a level of infection with Puccinia of 100%.

Example B2

Action Against *Cercospora arachidicola* on Peanut Plants (Curative Action)

Two peanut plants cv. "Tamnut" in the 4-leaf stage are sprayed with a conidia suspension of *Cercospora arachidicola* (approx. 200,000 conidia/ml) and subsequently incubated at 25–26° C. and under dew-point conditions. After two days, the plants are sprayed thoroughly from all sides with a spray mixture prepared with a wettable powder of the active substance (with 160 ppm of active ingredient). The treated plants are subsequently incubated in a controlled-environment cabinet under the following conditions: 25–27° C. and 80% atmospheric humidity during the day, 20° C. and dew-point conditions during the night; the photoperiod in each case is 16 hours. 12 days after the treatment, the test is evaluated by determining the leaf area infected with *Cercospora arachidicola* as a percentage compared with the infected control.

Compared with untreated, but infected control plants (number and size of lesions=100%), peanut plants which have been treated with active substances from the tables showed a highly reduced level of infection with Cercospora.

The following compounds, for example, show an action of more than 75% when used at a dosage rate of 160 ppm: 3, 8, 9, 10, 11, 12, 13, 14, 17, 19, 22, 24, 25, 26, 30, 32, 33, 34, 36, 38, 40, 41, 44, 49, 52, 66, 68, 71, 83, 90, 101, 129, 130, 133, 138, 145, 148.

Example B3

*Erysiphe graminis* (Protective Action)

30–40 wheat seedlings cv. "Lita" in the 1-leaf stage (distributed to two pots of ⌀7 cm) are sprayed thoroughly with a spray mixture prepared with a wettable powder of the active substance (with 160 ppm of active ingredient) and then cultured further in the greenhouse. One day after the treatment, the plants are dusted with conidia of *Erysiphe graminis*. The test is evaluated 7 days after the infection by determining the size of the leaf area covered in *Erysiphe graminis* as a percentage compared with the infected control.

The following compounds, for example, show an action of more than 75% when used at a dosage rate of 160 ppm:

1, 3, 4, 5, 7A, 8, 9, 10, 11, 13, 15, 16, 18, 23, 24, 25, 27, 29, 31, 33, 34, 37, 39, 40, 52, 53, 70, 86, 89, 105, 119, 120, 126, 127, 128, 135, 137, 141, 149.

Untreated, but infected control plants show a level of infection with Erysiphe of 100%.

Example B4

*Venturia inaequalis* (Curative Action)

Two apple seedlings cv. "Golden Delicious" are sprayed with a conidia suspension of *Venturia inaequalis* and subsequently incubated at 18° C. and under dew-point conditions. After 24 hours, the plants are sprayed thoroughly from all sides with a spray mixture prepared with a wettable powder of the active substance (with 50 ppm of active ingredient). The treated apple seedlings are subsequently cultured further in the greenhouse. 9–10 days after the treatment, the test is evaluated by determining the leaf area covered in *Venturia inaequalis* as a percentage compared with the infected control.

The following compounds, for example, show an action of more than 75% when used at a dosage rate of 50 ppm: 1, 3, 7A, 8, 9, 10, 12, 13, 14, 15, 17, 19, 20, 22, 24, 28, 29, 30, 31, 32, 33, 34, 36, 38, 44, 49, 54, 61, 64, 66, 78, 82, 83, 85, 105, 106, 117, 124, 131, 134, 135, 139, 142, 147, 154, 157.

Example B5

*Alternaria brassicae* (Protective Action)

4 cabbage seedlings, cv. "Vorbote", in the 6-leaf stage, distributed to 2 pots, are sprayed thoroughly with a spray mixture prepared with a wettable powder of the active substance (with 50 ppm of active ingredient) and subsequently cultured further in a controlled-environment cabinet at 19° C. and with 16 hours illumination per day. Two days after the treatment, the plants are infected by spraying with an aqueous conidia suspension (approx. 30,000 conidia/ml). The cabbage plants are then incubated at 24–26° C., under dew-point conditions and with a photoperiod of 16 hours. The test is evaluated 2–5 days after the infection by determining the leaf area infected with *Alternaria brassicae* as a percentage compared with the infected, untreated control.

The following compounds, for example, show an action of more than 75% at a dosage rate of 50 ppm: 1, 3, 4, 8, 9, 12, 13, 14, 17, 20, 22, 23, 24, 25, 26, 28, 29, 30, 31, 32, 33, 34, 36, 38, 54, 55, 67, 92, 105, 124, 130, 136, 138, 143, 150, 157.

Example B6

Action against *Phytophthora infestans* on Tomatoes a) Curative Action

After a raising period of three weeks, tomato plants cv. "Roter Gnom" are sprayed with a zoospore suspension of fungus and incubated in a cabinet at 18 to 20° C. and saturated atmospheric humidity. The humidification is interrupted after 24 hours. After the plants have dried, they are sprayed with a mixture which contains the active substance, formulated as a wettable powder, at a concentration of 200 ppm. After the spray coating has dried on, the plants are returned to the humid cabinet for 4 days. Number and size of the typical lesions which have developed after this period are used as a scale for assessing the activity of the tested substances.

b) Preventive-systemic Action

The active substance, formulated as a wettable powder at a concentration of 60 ppm (relative to the soil volume) is placed on the soil surface of potted tomato plants, aged three weeks, cv. "Roter Gnom". After a waiting period of three days, the underside of the leaves of the plants is sprayed with a zoospore suspension of *Phytophthora infestans*. They are then kept for 5 days in a spray cabinet at 18 to 20° C. and saturated atmospheric humidity. After this time, typical lesions develop, whose number and size is used for assessing the activity of the tested substances.

Compounds from Tables 1–3 effect inhibition of the disease level to less than 20%.

Example B7

*Plasmopara viticola* (Protective Action)

2 grapevine seedlings cv. Riesling×Sylvaner, each in the 4–5 leaf stage, are sprayed thoroughly from all sides with a spray mixture prepared with a wettable powder of the active substance (with 160 ppm of active ingredient) and subsequently cultured further in a controlled-environment cabinet at 17° C., 70–80% relative atmospheric humidity and with a photoperiod of 16 hours. After 6 days, the test plants are infected by spraying the undersides of the leaves with zoosporangia of *Plasmopara viticola*, suspended in distilled water (approx. 300,000 sporangia/ml). The grapevine plants are then incubated as follows: 1 day at 22° C. and under dew-point conditions in the dark and subsequently 4 days in the greenhouse. To induce fructification of *Plasmopara viticola*, the grapevines are transferred to a controlled-environment cabinet with dew-point conditions at 22° C. on day 5 after the infection.

The tests are carried out in each case on day 6 after the infection by determining the leaf area infected with *Plasmopara viticola* as a percentage compared with the infected, untreated control.

The following compounds, for example, show an action of more than 75% at a dosage rate of 160 ppm: 3, 4, 8, 9, 11, 12, 17, 22, 24, 28, 29, 30, 31, 32, 36, 38, 41, 43, 45, 53, 61, 62, 82, 102, 107, 120, 125, 129, 135, 138, 147, 150.

What is claimed is:

1. A compound of the formula:

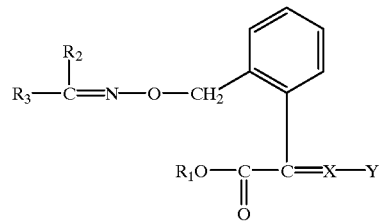

wherein
  $R_1$ is alkyl of 1 to 4 carbon atoms;
  X—Y is =NOCH$_3$ or =NOC$_2$H$_5$;
  $R_2$ is hydrogen, alkyl of 1 to 4 carbon atoms, haloalkyl of 1 to 4 carbon atoms, cycloalkyl of 3 to 6 carbon atoms, alkenyl of 2 to 4 carbon atoms, alkynyl 2 to 4 carbon atoms, methoxymethyl, ethoxymethyl, methylthiomethyl, ethylthiomethyl, alkylsulfonyl of 1 to 4 carbon atoms, alkoxy of 1 to 3 carbon atoms, alkylthio of 1 to 3 carbon atoms, or cyano;
  $R_3$ is heteroarylalkyl of 1 to 4 carbon atoms which is substituted or unsubstituted, heteroaryloxyalkyl of 1 to 4 carbon atoms which is substituted or unsubstituted, heteroarylalkenyl of 2 to 4 carbon atoms which is substituted or unsubstituted, heteroaryl which is substituted or unsubstituted, or heteroaroyl which is substituted or unsubstituted;

or $R_2$ and $R_3$ together with the carbon atom to which they are bound form a 4 to 6 membered saturated or unsaturated ring containing O, S, or N and which can additionally have a substituted or unsubstituted fused benzene ring.

2. A compound according to claim 1 wherein $R_1$ is methyl;

X—Y is =NOCH$_3$;

$R_2$ is hydrogen, methyl, ethyl, n-propyl, i-propyp, trifluoromethyl, methoxymethyl, cyclopropyl, allyl, cyano, methylsulfonyl, methylsulfonylmethyl, t-butyl, methylthio, or methoxy; and $R_3$ is 3,4-methylenedioxyphenyl, 3,4-ethylenedioxyphenyl, 3,4-propylenedioxyphenyl, 3,4-(2,2-dimethylpropylenedioxy)phenyl, 3,4-isopropylidenedioxyphenyl, 3,4-methoxymethylenedioxyphenyl, 6-nitro-3,4-methylenedioxyphenyl, 2,3-difluoromethylenedioxyphenyl, 3,4-benzylidenedioxyphenyl, 3,4-ethylenedioxybenzyl, 3,4-methylenedioxybenzyl, 1-(3,4-methoxymethylenedioxyphenyl)ethyl, 1-methyl-1-(3,4-methoxymethylenedioxyphenyl)ethyl, 3,4-methylenedioxyphenoxymethyl, 2-(3,4-methylenedioxyphenyl)ethyl, 2-(3,4-methylenedioxyphenyl)ethenyl, 1-(3,4-methylenedioxyphenyl)prop-1-en-2-yl, 1-chloro-1-(3,4-methylenedioxyphenyl)prop-1-en-2-yl, 3,4-methylenedioxybenzoyl, 2-thienyl, 2-(5-methylthienyl), 2-(5-chlorothienyl), 3-(2,5-dimethylthienyl), 2-thienoyl, 2-furyl, 2-pyridyl, 2-benzofuryl, 5-(2-cyanobenzofuryl), 5-(2-oxobenzofuryl), 5-(3-oxobenzofuryl), 6-(1,4-benzodioxanyl), 8-methoxy-6-(1,3-benzodioxanyl), or 2,2,3-trifluoro-6-(1,4-benzodioxanyl).

3. The compound according to claim 1 wherein $R_1$ is methyl;

X—Y is =NOCH$_3$;

$R_2$ is methyl; and $R_3$ is 2-thienyl.

4. The compound according to claim 1 wherein $R_1$ is methyl;

X—Y is =NOCH$_3$;

$R_2$ is methyl; and $R_3$ is 2-pyridyl.

5. A fungicidal composition comprising an effective amount of a compound according to claim 1 in combination with a suitable carrier therefor.

6. A method for controlling or preventing phytofungal attack which comprises application of an effective amount of a compound according to claim 1 to plants, parts of plants, or to the locus liable to be infected.

* * * * *